US007033520B2

(12) United States Patent
Kappel et al.

(10) Patent No.: US 7,033,520 B2
(45) Date of Patent: *Apr. 25, 2006

(54) METAL CHELATING COMPOSITIONS FOR PROTEIN PURIFICATION, DETECTION OR BINDING

(75) Inventors: William K. Kappel, Oakville, MO (US); Venkatappa Viswanatha, Ballwin, MO (US); Handong Li, St. Louis, MO (US); Richard J. Mehigh, Oakville, MO (US); John G. Dapron, Oakville, MO (US)

(73) Assignee: Sigma-Aldrich Co., Highland, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/667,928

(22) Filed: Sep. 22, 2003

(65) Prior Publication Data

US 2004/0092031 A1 May 13, 2004

Related U.S. Application Data

(63) Continuation of application No. 09/558,001, filed on Apr. 24, 2000, now Pat. No. 6,623,655.

(51) Int. Cl.
*C09K 3/00* (2006.01)

(52) U.S. Cl. .................. 252/1; 252/390; 436/166; 436/86; 562/512; 562/553; 562/571

(58) Field of Classification Search .............. 252/1, 252/390; 436/166, 86; 562/512, 553, 571
See application file for complete search history.

(56) References Cited

U.S. PATENT DOCUMENTS

| 2,205,995 | A | 6/1940 | Ulrich et al. |
| 2,885,428 | A | 5/1959 | Luskin |
| 3,337,607 | A | 8/1967 | Wollensak |
| 3,959,342 | A | 5/1976 | Homberg et al. |
| 4,569,794 | A | 2/1986 | Smith et al. |
| 4,664,806 | A | 5/1987 | Merz |
| 4,677,027 | A | 6/1987 | Porath et al. |
| 4,877,830 | A | 10/1989 | Dobeli et al. |
| 5,047,513 | A | 9/1991 | Dobeli et al. |
| 5,284,933 | A | 2/1994 | Dobeli et al. |
| 5,514,363 | A | 5/1996 | Shochat et al. |
| 5,625,075 | A | 4/1997 | Srinivasan et al. |

(Continued)

FOREIGN PATENT DOCUMENTS

| EP | 0 189 373 A2 | 7/1986 |
| EP | 0 253 303 A2 | 1/1988 |
| WO | WO 93/11735 A1 | 6/1993 |

OTHER PUBLICATIONS

Schmitt et al., "Affinity Purification of Histidine-tagged Proteins", Molecular Biology Reports, 1993, pp. 223-230, vol. 18.
Porath et al., "Immobilized Metal Ion Affinity Adsorption and Immobilized Metal Ion Affinity Chromatography of Biomaterials. Serum Protein Affinities for Gel-Immobilized Iron and Nickel Ions", Biochemistry, 1983, pp. 1621-1630, vol. 22.
Sulkowski, "Immobilized Metal Ion Affinity Chromatography of Proteins", Protein Purification: Micro to Macro pp. 149-162, Edited by R. Burgess, Published by Liss New York, NY.
International Search Report from analogous PCT application No. PCT/US01/11529 dated Oct. 16, 2001.
Lonnerdal et al., Journal of Applied Biochemistry, 1983, p. 203, vol. 4.
Porath et al., "Metal Chelate Affinity Chromatography, a New Approach to Protein Fractionation", Nature, Dec. 18, 1975, pp. 598-599, vol. 258.
Hochuli et al., "New Metal Chelate Adsorbent Selective for Proteins and Peptides Containing Neighbouring Histidine Residues", Journal of Chromatography, 1987, pp. 177-184, vol. 411.

(Continued)

*Primary Examiner*—Monique T. Cole
(74) *Attorney, Agent, or Firm*—Senniger Powers

(57) ABSTRACT

A metal chelating composition having the formula:

$$Q-S^1-L-N\begin{matrix}(CH_2)_i-Y\\ \\(CH_2)_i-Z\end{matrix}$$

wherein
  Q is a carrier;
  $S^1$ is a spacer;
  L is -A-T-CH(X)— or —C(=O)—;
  A is an ether, thioether, selenoether, or amide linkage;
  T is a bond or substituted or unsubstituted alkyl or alkenyl;
  X is —$(CH_2)_kCH_3$, —$(CH_2)_kCOOH$, —$(CH_2)_kSO_3H$, —$(CH_2)_kPO_3H_2$, —$(CH_2)_kN(J)_2$, or —$(CH_2)_kP(J)_2$, preferably —$(CH_2)_kCOOH$ or —$(CH_2)_kSO_3H$;
  k is an integer from 0 to 2;
  J is hydrocarbyl or substituted hydrocarbyl;
  Y is —COOH, —H, —$SO_3H$, —$PO_3H_2$, —$N(J)_2$, or —$P(J)_2$, preferably, —COOH;
  Z is —COOH, —H, —$SO_3H$, —$PO_3H_2$, —$N(J)_2$, or —$P(J)_2$, preferably, —COOH; and
  i is an integer from 0 to 4, preferably 1 or 2.

23 Claims, No Drawings

U.S. PATENT DOCUMENTS 5,747,663 A     5/1998    Colpan et al.
5,834,224 A    11/1998    Ruger et al.
5,990,301 A    11/1999    Colpan et al.
6,623,655 B1 *   9/2003    Kappel et al. ................. 252/1

OTHER PUBLICATIONS

Partial International Search Report from analogous PCT application No. PCT/US01/11529.

Janknecht et al., "Rapid and Efficient Purification of Native Histidine-tagged Protein Expressed by Recombinant Vaccinia Virus", Proc. Natl. Acad. Sci. USA, Oct., 1991, pp. 8972-8976, vol. 88.

F. Anspach, "Silica-based metal chelate affinity sorbents I. Preparation and characterization of iminodiacetic acid affinity sorbents prepared via different immbolization techniques", Journal of Chromatography A, 1994, pp. 35-49, vol. 672.

* cited by examiner

METAL CHELATING COMPOSITIONS FOR PROTEIN PURIFICATION, DETECTION OR BINDING

REFERENCE TO RELATED APPLICATION

This application is a continuation of U.S. Ser. No. 09/558,001, filed on Apr. 24, 2000, now U.S. Pat. No. 6,623,655, issued Sep. 23, 2003.

BACKGROUND OF THE INVENTION

The present invention is generally directed to metal chelating compositions and to methods for making and using the same for protein purification, detection or binding and, in particular, to nitrilotriacetic acid derivatives that have improved binding specificity and stability and to methods for making and using these nitrilotriacetic acid derivatives for protein purification, protein detection or protein binding.

Metal chelate affinity chromatography has been used as a technique for the purification of proteins for many years. Early resins used in this process were simple chelators such as iminodiacetic acid (IDA) coupled to agarose supports (Porath et al. *Nature*, 258:598–599, 1975) and charged with various metals such as $Cu^{2+}$, $Zn^{2+}$ and $Ni^{2+}$. These resins were found to selectively capture proteins and peptides from natural sources (Porath and Olin, *Biochemistry*, 22:1621, 1983; Lonnerdal and Keen, *J. Appl. Biochem.*, 4:203, 1983; Sulkowski, *Protein Purification: Micro to Macro*, pages 149–162, Edited by R. Burgess, Published by Liss New York, N.Y., 1987). With the advent of molecular biological techniques, metal chelate chromatography assumed a more important role in the purification of proteins with the use of a 6-histidine tag. See, for example, Dobeli et al., U.S. Pat. No. 5,284,933. The poly histidine tag bound very strongly to the immobilized nickel and could be used for the identification and purification of these recombinant molecules. The tridentate chelator IDA was quite selective for these tagged proteins but the nickel was found to leach slowly from the resin reducing the capacity and causing interference with some downstream uses of the proteins.

More recently, a tetradentate chelator known as nitrilotriacetic acid resin was developed for use with metals having six coordination sites. This resin has become the preferred resin for the purification of poly histidine containing proteins since it has very little metal leaching and good selectivity. However, considerable amount of effort is required to obtain this selectivity. For example, the addition of various amounts of imidazole is necessary to determine whether protein must be optimized to achieve the desired results (Janknecht et all, *Proc. Natl. Acad. Sci.*, 88:8972–8976, 1991, Schmitt et all., *Molecular Biology Reports*, 88:223–230, 1993).

In U.S. Pat. No. 4,877,830, Dobeli et al. describe nitrilotriacetic acid resins suitable for protein purification represented by the general formula:

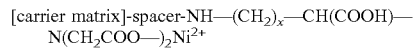

wherein x is 2, 3 or 4, the carrier matrix is one used in affinity or gel chromatography such as cross-linked dextrans, agarose or polyacrylamides, and the spacer is preferably —O—CH$_2$—CH(OH)—CH$_2$— or —O—CO—. Dobeli et al., U.S. Pat. No. 4,877,830 at col. 2, lines 23–37. These resins are prepared by reacting an N-terminal protected compound of the formula:

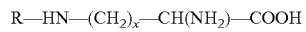

wherein R is an amino protecting group and x is 2,3 or 4, with bromoacetic acid in an alkaline medium and subsequently cleaving off the protecting group and reacting this product with an activated resin. See, e.g., Hochuli et al., *Journal of Chromatography*, 411(1987) 177–184.

In U.S. Pat. No. 5,625,075, Srinivasan et al. describe a metal radionuclide chelating compound having multiple sulfur and nitrogen atoms. These chelating compounds incorporate two nitrogen atoms and three sulfur atoms, two nitrogen atoms and four sulfur atoms, or three nitrogen atoms and three sulfur atoms.

While these compounds provide improved specificity relative to some resins containing nitrilotriacetic acid derivatives, a need remains for chelating compounds having greater binding specificity for polyhistidine containing proteins.

SUMMARY OF THE INVENTION

Among the objects of the present invention is the provision of metal chelating compositions and to metal chelates which are relatively stable and provide superior binding specificity for protein or polypeptide purification, protein or polypeptide detection or protein or polypeptide binding, and the provision of processes for the preparation and use of such compositions.

Briefly, therefore, the present invention is directed to a metal chelating composition having the formula:

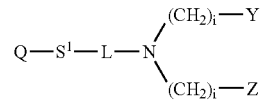

wherein
Q is a carrier;
$S^1$ is a spacer;
L is -A-T-CH(X)— or —C(=O)—;
A is an ether, thioether, selenoether, or amide linkage;
T is a bond or substituted or unsubstituted alkyl or alkenyl;
X is —(CH$_2$)$_k$CH$_3$, —(CH$_2$)$_k$COOH, —(CH$_2$)$_k$SO$_3$H, —(CH$_2$)$_k$PO$_3$H$_2$, —(CH$_2$)$_k$N(J)$_2$, or —(CH$_2$)$_k$P(J)$_2$;
k is an integer from 0 to 2;
J is hydrocarbyl or substituted hydrocarbyl;
Y is —COOH, —H, —SO$_3$H, —PO$_3$H$_2$, —N(J)$_2$, or —P(J)$_2$;
Z is —COOH, —H, —SO$_3$H, —PO$_3$H$_2$, —N(J)$_2$, or —P(J)$_2$; and
i is an integer from 0 to 4.

The present invention is further directed to a metal chelate comprising a metal and the metal chelating composition of the present invention.

The present invention is further directed to a process for the purification or detection of a polypeptide or other composition having an affinity for a metal chelate. The process comprising contacting the composition with a metal chelate, the metal chelate comprising a metal and the metal chelating composition of the present invention.

The present invention is further directed to a process for the preparation of a mono- or dicarboxylated amine. The process comprises combining an amine and an oxoacid in the presence of a reducing agent. The amine has the formula $R^2R^3NH$ wherein $R^2$ is hydrocarbyl or substituted hydrocarbyl and $R^3$ is hydrogen, hydrocarbyl or substituted hydrocarbyl.

Other objects and features will be in part apparent and in part pointed out hereinafter.

DETAILED DESCRIPTION OF THE PREFERRED EMBODIMENTS

The linkage between the chelator and the resin was found by us to be an important parameter for the selectivity of the resin for polyhistidine tagged proteins. Conventional nitrilotriacetic acid resin has a positively charged amine linkage that acts as a binding site for any negatively charged molecule which may interfere with the binding of the protein to the coordination sites offered by the immobilized metal. Oxygen, sulfur, selenium and amides have some affinity for metals which may provide enhanced chelation properties, binding the metal more firmly than traditional tetradentate chelators having positive amine linkages. In addition, the use of a non-charged atoms between the nitrilo nitrogen and the carrier appears to reduce non-specific binding of proteins.

The metal chelating compositions of the present invention are capable of forming relatively stable chelates with metal ions and, advantageously, the presence of ether (—O—), thioether (—S—), selenoether (—Se—) or amide ((—$NR^1$(C=O)—) or (—(C=O)$NR^1$—) wherein $R^1$ is hydrogen or hydrocarbyl) linkages within the chelating composition contributes to the specificity of the resulting chelate when it is used for the separation or purification of molecules such as proteins, phosphoproteins, peptides, phosphopeptides, DNA, RNA, oligonucleotides, drugs, and synthetic and natural products that have an affinity for metal chelates such as clustered histidines or poly histidines.

In general, the chelating compositions of the present invention correspond to composition (1) shown in the structure below:

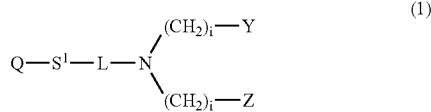

wherein
Q is a carrier;
$S^1$ is a spacer;
L is -A-T-CH(X)— or —C(=O)—;
A is an ether, thioether, selenoether, or amide linkage;
T is a bond or substituted or unsubstituted alkyl or alkenyl;
X is —$(CH_2)_kCH_3$, —$(CH_2)_kCOOH$, —$(CH_2)_kSO_3H$, —$(CH_2)_kPO_3H_2$, —$(CH_2)_kN(J)_2$, or —$(CH_2)_kP(J)_2$, preferably —$(CH_2)_kCOOH$ or —$(CH_2)_kSO_3H$;
k is an integer from 0 to 2;
J is hydrocarbyl or substituted hydrocarbyl;
Y is —COOH, —H, —$SO_3H$, —$PO_3H_2$, —$N(J)_2$, or —$P(J)_2$, preferably, —COOH;
Z is —COOH, —H, —$SO_3H$, —$PO_3H_2$, —$N(J)_2$, or —$P(J)_2$, preferably, —COOH; and
i is an integer from 0 to 4, preferably 1 or 2.

In general, the carrier, Q, may comprise any solid or soluble material or compound capable of being derivatized for coupling. Solid (or insoluble) carriers may be selected from a group including agarose, cellulose, methacrylate copolymers, polystyrene, polypropylene, paper, polyamide, polyacrylonitrile, polyvinylidene, polysulfone, nitrocellulose, polyester, polyethylene, silica, glass, latex, plastic, gold, iron oxide and polyacrylamide, but may be any insoluble or solid compound able to be derivatized to allow coupling of the remainder of the composition to the carrier, Q. A preferred solid carrier is agarose or a high-throughput screening microtiterplate. Soluble carriers include proteins, nucleic acids including DNA, RNA, and oligonucleotides, lipids, liposomes, synthetic soluble polymers, proteins, polyamino acids, albumin, antibodies, enzymes, streptavidin, peptides, hormones, chromogenic dyes, fluorescent dyes, flurochromes or any other detection molecule, drugs, small organic compounds, polysaccharides and any other soluble compound able to be derivatized for coupling the remainder of the composition to the carrier, Q. Proteins or polysaccharides are the preferred carrier.

The spacer, $S^1$, which flanks the carrier comprises a chain of atoms which may be saturated or unsaturated, substituted or unsubstituted, linear or cyclic, or straight or branched. Typically, the chain of atoms defining the spacer, $S^1$, will consist of no more than about 25 atoms; stated another way, the backbone of the spacer will consist of no more than about 25 atoms. More preferably, the chain of atoms defining the spacer, $S^1$, will consist of no more than about 15 atoms, and still more preferably no more than about 12 atoms. The chain of atoms defining the spacer, $S^1$, will typically be selected from the group consisting of carbon, oxygen, nitrogen, sulfur, selenium, silicon and phosphorous and preferably from the group consisting of carbon, oxygen, nitrogen, sulfur and selenium. In addition, the chain atoms may be substituted or unsubstituted with atoms other than hydrogen such as hydroxy, keto (=O), or acyl such as acetyl. Thus, the chain may optionally include one or more ether, thioether, selenoether, amide, or amine linkages between hydrocarbyl or substituted hydrocarbyl regions. Exemplary spacers, $S^1$, include methylene, alkyleneoxy (—$(CH_2)_aO$—), alkylenethioether (—$(CH_2)_aS$—), alkyleneselenoether (—$(CH_2)_aSe$—), alkyleneamide (—$(CH_2)_aNR^1(C=O)$—), alkylenecarbonyl (—$(CH_2)_aCO$)—, and combinations thereof wherein a is generally from 1 to about 20 and $R^1$ is hydrogen or hydrocarbyl, preferably alkyl. In one embodiment, the spacer, $S^1$, is a hydrophilic, neutral structure and does not contain any amine linkages or substituents or other linkages or substituents which could become electrically charged during the purification of a polypeptide.

As noted above, the linker, L, may be -A-T-CH(X)— or —C(=O)—. When L is -A-T-CH(X)—, the chelating composition corresponds to the formula:

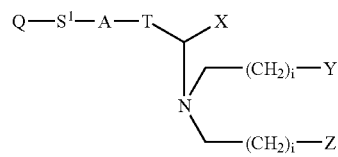

wherein Q, $S^1$, A, T, X, Y, and Z are as previously defined. In this embodiment, the ether (—O—), thioether (—S—), selenoether (—Se—) or amide ((—$NR^1$(C=O)—) or (—(C=O)$NR^1$—) wherein $R^1$ is hydrogen or hydrocarbyl) linkage is separated from the chelating portion of the molecule by a substituted or unsubstituted alkyl or alkenyl region. If other than a bond, T is preferably substituted or unsubstituted $C_1$ to $C_6$ alkyl or substituted or unsubstituted $C_2$ to $C_6$ alkenyl. More preferably, A is —S—, T is —$(CH_2)_n$—, and n is an integer from 0 to 6, typically 0 to 4, and more typically 0, 1 or 2.

When L is —C(=O)—, the chelating composition corresponds to the formula:

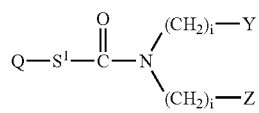

wherein Q, $S^1$, i, Y, and Z are as previously defined.

In a preferred embodiment of the present invention, the sequence —$S^1$-L-, in combination, is a chain of no more than about 35 atoms selected from the group consisting of carbon, oxygen, sulfur, selenium, nitrogen, silicon and phosphorous, more preferably only carbon, oxygen sulfur and nitrogen, and still more preferably only carbon, oxygen and sulfur. To reduce the prospects for non-specific binding, nitrogen, when present, is preferably in the form of an amide moiety. In addition, if the carbon chain atoms are substituted with anything other than hydrogen, they are preferably substituted with hydroxy or keto. In a preferred embodiment, L comprises a portion (sometimes referred to as a fragment or residue) derived from an amino acid such as cystine, homocystine, cysteine, homocysteine, aspartic acid, cysteic acid or an ester thereof such as the methyl or ethyl ester thereof.

Exemplary chelating compositions of the present invention include the following:

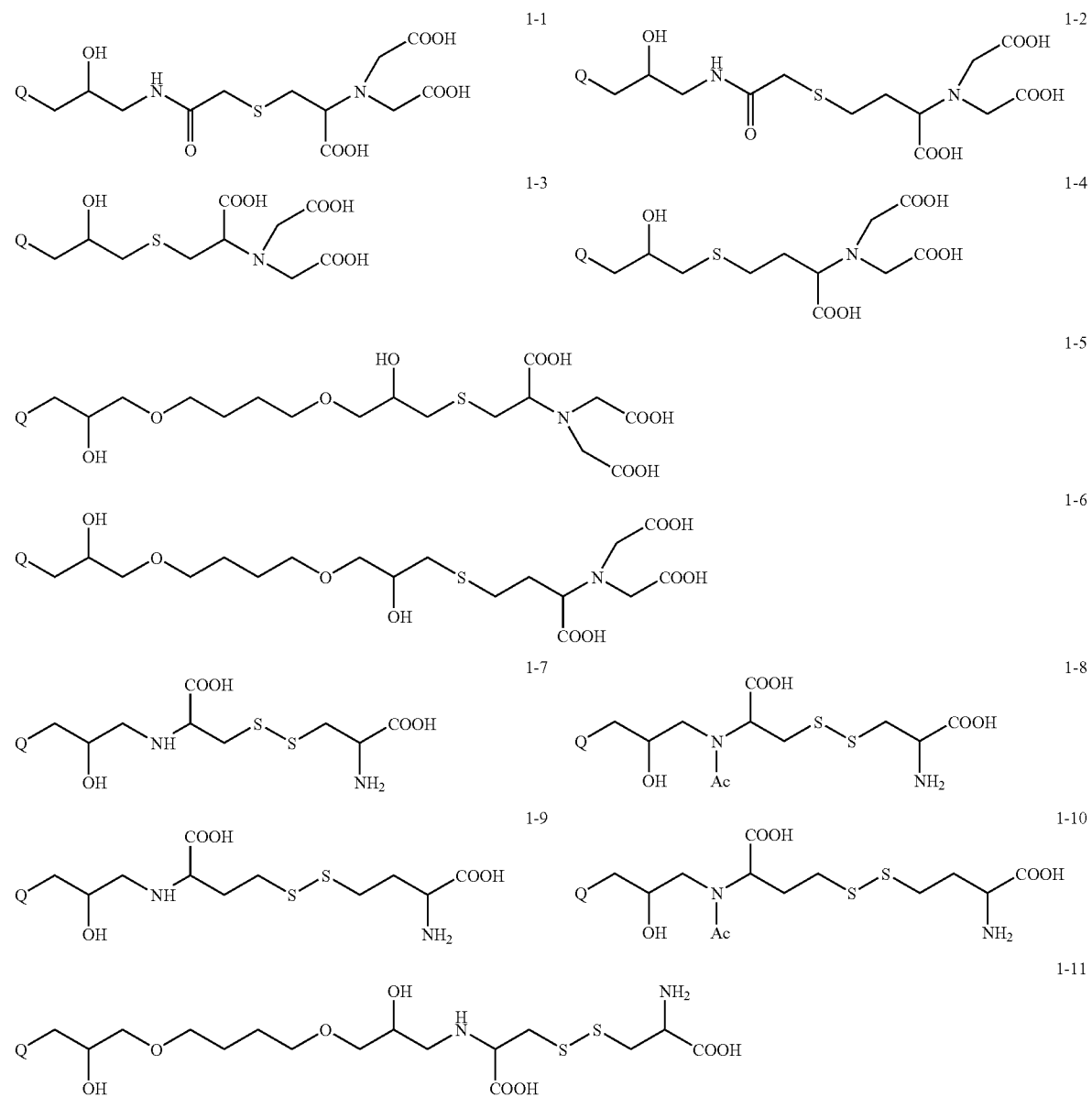

-continued
1-12
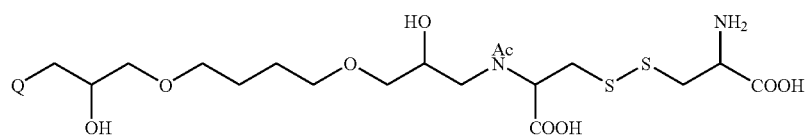
1-13
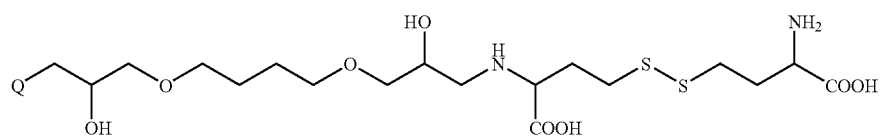
1-14
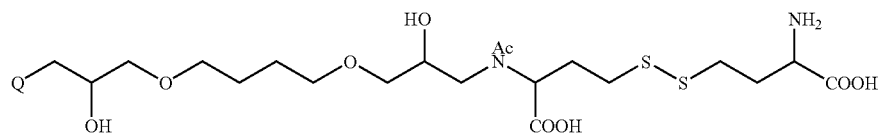
1-15
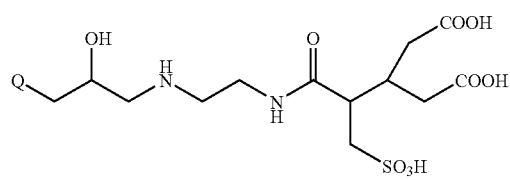
1-16
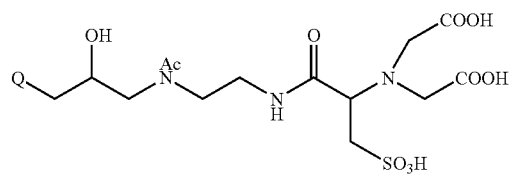
1-17
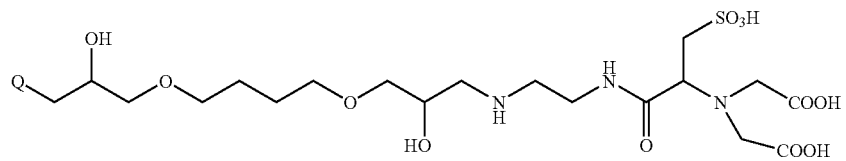
1-18
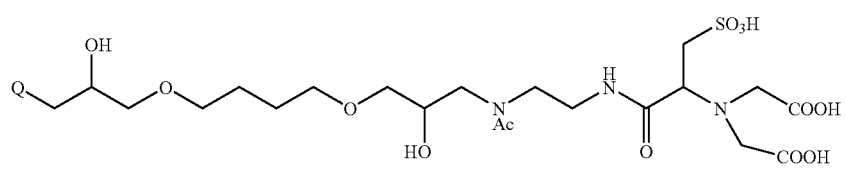
1-19
1-20
1-21
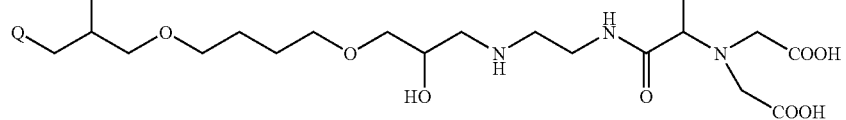
1-22
1-23
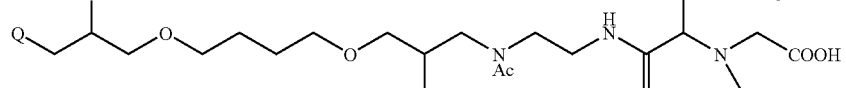
1-24
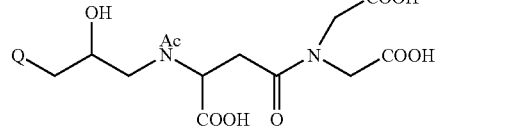

-continued

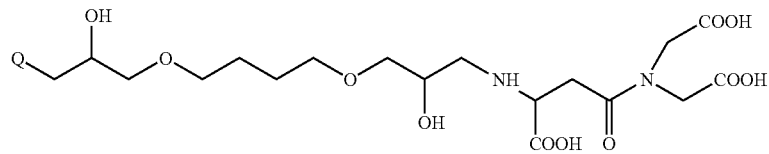
1-25

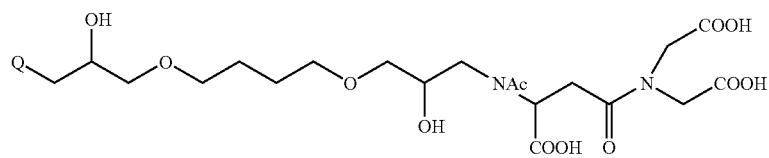
1-26 wherein Q is a carrier and Ac is acetyl.

Advantages are gained by the use of neutral ether, thioether, selenoether or amide linkage(s) in the linking moiety instead of positively charged amine linkages. Oxygen, sulfur, and selenium atoms and amides have some affinity for metals which may provide enhanced chelation properties, binding the metal more firmly than traditional tetradentate chelators having positive amine linkages. In addition, the use of a non-charged atoms between the nitrilo nitrogen and the carrier appears to reduce non-specific binding of proteins. Use of S, O, Se or amide in the linking moiety, L, therefore, in place of amine or other charged moieties tends to increase the stability and specificity of the composition for protein purification.

In one embodiment, metal chelating compositions (1) of the present invention may be derived from compositions having the general formula:

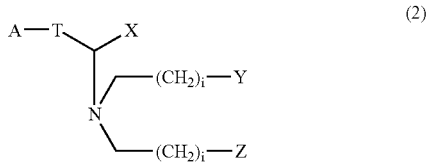
(2)

wherein A, T, X, Y, Z and i are as previously defined. Preferably, composition (2) is represented by one of the following formulae:

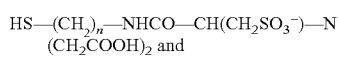 and

wherein n is 1 or 2.

Compositions corresponding to structure (2) in which at least one of X, Y and Z comprises a carboxylic acid moiety may be prepared by reductive alkylation of an amine. In general, mono- and dicarboxylated amines may be prepared by reacting an amine having the formula $R^2R^3NH$ wherein $R^2$ is hydrocarbyl or substituted hydrocarbyl and $R^3$ is hydrogen, hydrocarbyl or substituted hydrocarbyl with an oxoacid, such as glyoxylic acid, in the presence of a reducing agent such as a pyridine-borane complex, dimethylborane, trimethylborane, sodium cyanoborohydride. When the amine is an amino acid such as cystine, homocystine, cysteine, homocysteine, aspartic acid, cysteic acid or an ester thereof such as the methyl or ethyl ester thereof, the reaction advantageously produces a nitrilotriacetic acid derivative. For example, a nitrilotriacetic acid derivative of cystine may be prepared by combining cystine, an oxoacid such as glyoxylic acid, and a mild reducing agent; alcohol may preferably be included to aid in the clarification of the solution. Alternatively, other methods known in the art may be used for the preparation of composition (2), including haloalkylacids.

Composition (2) may be immobilized to form composition (1) by covalently attaching a chemical spacer, $S^1$, to the linker, L, by any method known in the art and then reacting the carrier with the spacer, $S^1$, to form a carrier-spacer chelate complex of composition (1). In another embodiment, carrier Q is first reacted with the spacer, $S^1$, to form a carrier-spacer complex. Thereafter, the carrier-spacer complex is attached to the chelate-complex through the linker, L, to form composition (1).

In some instances, it is advantageous to activate the carrier, Q, with $S^1$ prior to the attachment of the chelating portion of the molecule. In these instances where Q is an agarose resin, it may be activated using epichlorohydrin, tetrabutyldiglycidyl ether or any substance capable of activating a carrier.

A metal chelate may be formed by addition of a metal or a metal oxide to chelating composition (1) or composition (2) of the present invention. For example, a metal chelate of the present invention (in immobilized form) is represented by the following formula:

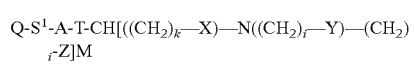

wherein Q, $S^1$, A, i, J, k, T, X, Y, and Z are as defined above and M comprises any metal or metal oxide capable of forming a chelate. Preferred metals and metal oxides include Ni, Hg, Ga, Cu, Ru, Co, Cd, Mg, Mn, Ti, In, Zn, Tc, Rh, Pd, Re, Fe, Au, Pb, and Bi, with Fe, Cu, Co, Au, and Ni being preferred for most applications. In general, the metal, M, preferred for a given application is dependant upon the specific binding capabilities of the chelating portion of composition (1) or (2) and on the compound to be bound or purified. For example, when X, Y and Z are —COOH, M is optimally Ni for purifying proteins with poly histidine sequences. When the compound is a phophoprotein, a phosphopeptide or a phosphate containing molecule, M is optimally Fe or Ga.

Definitions

The "hydrocarbyl" moieties described herein are organic compounds or radicals consisting exclusively of the elements carbon and hydrogen. These moieties include alkyl, alkenyl, alkynyl, and aryl moieties. These moieties may be substituted or unsubstituted and preferably are substituted or unsubstituted alkyl. These moieties also include alkyl, alkenyl, alkynyl, and aryl moieties substituted with other aliphatic or cyclic hydrocarbyl groups, such as alkaryl, alkenaryl and alkynaryl. Unless otherwise specified, these moieties comprise 1 to 20 carbon atoms.

Unless otherwise specified, the alkyl groups described herein are preferably lower alkyl containing from one to six carbon atoms in the principal chain and up to 20 carbon atoms. They may be straight, branched chain or cyclic and include methyl, ethyl, propyl, isopropyl, butyl, hexyl and the like. They may be substituted with aliphatic or cyclic hydrocarbyl radicals.

Unless otherwise specified, the alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbyl radicals.

Unless otherwise specified, the alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbyl radicals.

Unless otherwise specified, the aryl moieties described herein contain from 6 to 20 carbon atoms and include phenyl. They may be hydrocarbyl substituted with the various substituents defined herein. Phenyl is the more preferred aryl.

The substituted hydrocarbyl moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents are other than hydroxyl and include lower alkoxy such as methoxy, ethoxy, butoxy; halogen such as chloro or fluoro; ethers; acetals; ketals; esters; heteroaryl such as furyl or thienyl; alkanoxy; acyl; acyloxy; nitro; amino; and amido.

The acyl moieties described herein contain hydrocarbyl, substituted hydrocarbyl or heteroaryl moieties. They have the general formula —C(O)X wherein X may include hydrocarbyl, hydrocarbyloxy, hydrocarbylamino or hydrocarbylthio.

A protein, as used herein, includes antibodies, enzymes, hemoglobin, hormones, polypeptides and peptides; and may be an intact molecule, a fragment thereof, or a functional equivalent thereof; and may be genetically engineered.

An antibody, as used herein, includes both polyclonal and monoclonal antibodies; and may be an intact molecule, a fragment thereof; and may be genetically engineered.

The following examples illustrate the invention.

EXAMPLE 1

Preparation of N,N-bis(carboxymethyl)-L-cysteine coupled to an insoluble carrier via solid phase carboxymethylation Preparation of epichlorohydrin activated Sepharose®: 50 ml of Sepharose® CL 4B (Pharmacia Biotech) was washed three times with 100 ml of water in a glass suction filter. It was transferred into a 3-necked flask fitted with a stirrer and a thermometer. 30 ml of water and 4 ml of 10 N sodium hydroxide were added with stirring followed by 8 ml of epichlorohydrin. The mixture was heated at 46° C. for 2 hours. The activated resin was washed to a neutral pH using 800 ml of deionized water.

Preparation of N,N-bis-Carboxymethyl-L-cysteine Agarose: A solution of 16.3 g of L-cysteine in 185 ml of 1 N sodium hydroxide was added to 48 ml of epichlorohydrin activated resin in an Erlenmeyer flask and mixed gently for 18 hours at 22° C. The mixture was washed five times with 200 ml of water. The Kaiser test for free amine [Kaiser, E., et al, Anal. Biochem., 34:595 (1970)] gave a deep blue color. 47.6 ml of the above wet resin in an Erlenmeyer flask was mixed gently with a solution of 8.0 g of bromoacetic acid in 50 ml of 1 N sodium hydroxide and 25 ml of 1 M sodium bicarbonate for 72 hours at 22° C. The resin was then washed three times with 100 ml of deionized water. 16 g of wet resin was stirred gently with 50 ml of 0.2 M sodium acetate and 2.5 ml of acetic anhydride for 45 minutes at 22° C. The resin was washed three times with 100 ml of water. The Kaiser test gave faint blue color. The resin was stored in an equal volume of 30% ethanol at 4° C.

Nickel loading and capacity analysis: The N,N-bis(carboxymethyl)cysteine resin prepared as described above was first tested by determining the ability of the resin to chelate nickel. Approximately 2.5 ml of the resin was incubated with 10 ml of 10 mg/ml nickel sulfate over night with shaking at 50 rpm at 4° C. The resin was mixed well and placed into 1×10 cm column and the extra nickel solution was allowed to flow out of the resin. The unbound nickel sulfate was rinsed from the resin using 20 to 30 column volumes of deionized water. The remaining water was allowed to drain out of the resin. An equal volume of water was added to the resin, mixed well and then the slurry was removed from the column for storage at 4° C. The equivalent of one ml of packed bed resin was acid hydrolyzed and then analyzed by ICP for nickel content. This resin bound 5.2 µmole of nickel per ml of resin.

Protein binding and specificity testing: The use test for specific protein binding of poly histidine containing proteins was done on a 0.5×7.6 cm column containing 1.5 ml of packed bed resin. The resin was equilibrated with 50 mM sodium phosphate, 0.5 M sodium chloride and 10 mM imidazole pH 8.0 (equilibration buffer). Five ml of a crude E. coli extract containing a bacterial alkaline phosphatase with a poly-histidine tag was loaded onto the column. This crude extract was made fresh from frozen E. coli cell paste using CelLytic-B (Sigma Chemical Company). The column was washed with 10 column volumes (15 ml) of equilibration buffer to remove unbound proteins. The bound material was eluted with 10 column volumes (15 ml) 50 mM sodium phosphate, 0.5 M sodium chloride and 320 mM imidazole pH 8.0. The peak fractions of the eluted material were pooled. The eluted material was assayed for purity by sodium dodecyl sulfate polyacrylamide gel electrophoresis (SDS-PAGE), alkaline phosphatase activity and protein content by Bradford protein assay. The assay results demonstrated that the eluted protein from this one step isolation procedure using this unique chelate resin gave essentially homogeneous bacterial alkaline phosphatase.

EXAMPLE 2

Preparation of N,N-bis(carboxymethyl)-L-cystine

Preparation of N,N,N',N'-tetrakis(carboxymethyl)-L-cystine: L-cystine (24.03 g; 0.1 moles) was placed into a beaker containing 2.0 L of 0.05 M Borate buffer, pH 9.0 and mixed with a magnetic stir bar. Glyoxylic acid (monohydrate)

(368.2 g; 4 moles) was added to the solution with mixing. The solution contained 20 ml buffer per mmole cystine and 40 mole glyoxylic acid per mole cystine. An ice-water bath was placed around the beaker to cool the solution to between 15 to 25° C. The pH of the mixture was adjusted to 9.0 with 5 N sodium hydroxide. The ice-bath was removed and the beaker was left at room temperature. 8 M borane-pyridine complex (250 mL) was added, 20 moles per mole cystine. Ethanol to a final concentration of between 25 to 50% was added to clarify the solution. The solution was stirred at room temperature for two hours to complete the reaction. The reaction was monitored by HPLC until the reaction was complete. The reaction mixture was poured into a larger vessel and diluted with 3 volumes of water. Hydrochloric acid (10 N) was added slowly to adjust the pH to less than 1.0. The reaction mixture was stirred 30 to 60 minutes. The pH of the reaction mixture was then adjusted using 5 N sodium hydroxide to about 6.5.

Purification of N,N,N',N'-tetrakis(carboxymethyl)-L-cystine: The crude N,N,N',N'-tetrakis(carboxymethyl)-L-cystine reaction mix was diluted with water to lower the conductivity to less than 5 milli mhos. The pH was adjusted to between 7.0 and 8.5 with 1 M sodium hydroxide. The mixture was then applied to a DEAE-Sephadex®-HCO3 (Pharmacia Biotech) column that had been equilibrated in deionized water using 10 ml resin per mmole cystine starting material. When the column charge was complete, it was washed with 4 column volumes of deionized water. The column was then washed with 4 column volumes 0.1 M triethylammonium bicarbonate (TEAB). The purified product was eluted from the column with 0.5 M TEAB. The pooled material was dried in a Rotovap until a tacky solid was formed. It was then dissolved in a minimum volume of water. The material was now dried completely. The water resuspension and drying steps were then repeated once more. The final solid was dissolved in 400 mL water.

Conversion to the free acid: Amberlite IR H+ resin equilibrated with deionized water was added to the crude material (25 ml resin per mmole cystine). The pH was monitored with pH paper. After conversion to the free acid the resin was removed by filtration. The filtrate was dried in a Rotovap until completely dry.

Reduction of N,N,N',N'-tetrakis(carboxymethyl)-L-cystine to N,N-bis(carboxymethyl)-L-cysteine tetrakis(carboxymethyl)cystine: The crude tetrakis(carboxymethyl)-L-cystine (23.65 g, 0.05 moles) was dissolved in water at 5 ml water per gram. The pH of the solution was adjusted to 9.0 to 9.2 with 1 N sodium hydroxide. Then 14.34 g (0.05 moles) of tris(carboxyethyl)phosphine (TCEP) was added with stirring until all the TCEP dissolved. It was then incubated for 10 min. The reduction was followed by HPLC. After complete reduction, generally in less than 20 minutes, the pH was adjusted to 5.0 to 6.0 with 1 N hydrochloric acid. The product can be used at this point or it can be lyophilized. Yield was between 50–75% based on starting amount of cystine.

EXAMPLE 3

Preparation and analysis of N,N-bis(carboxymethyl)-L-cysteine covalently attached to agarose Epichlorohydrin activation of resin: 1 L of Sepharose® 6B (Pharmica Biotech) was washed well with deionized water. The resin was suspended in an equal volume of 0.8 M sodium hydroxide. It was the combined with 100 ml epichlorohydrin while mixing. The material was incubated for 2 hours at room temperature with mixing. The resin was washed with 3 volumes of 0.1 M sodium phosphate, pH 7 followed by 6 volumes of deionized water.

Resin amination: The amino Sepharose® 6B was prepared by suspending the epichlorohydrin activated resin in an equal volume (one resin volume) of 2 M ammonium hydroxide and gently mixed overnight at room temperature. The resin was washed with 3 volumes of 0.1 M sodium phosphate, pH 7. The resin was washed with 6 volumes of deionized water Bromoacetylation of amino Sepharose® 6B: The washed amino Sepharose® 6B resin was added to water to make a 50% resin slurry. The pH was adjusted to about 5.8 to 6.0 with 1 N HCl. The resin slurry was maitained at room temperature and the following reactions were conducted in reduced light conditions. 0.15 moles of bromoacetic acid in 0.2 M imidazole pH 5.8 was added to the slurry. Then 0.75 moles solid 1-ethyl-3-(3-diamethylaminopropyl)carbodiimide (EDAC) was added while the resin was being mixed gently. This resin slurry was gently mixed at room temperature for 4 hours while maintaining pH 6.0. The unreacted amines were blocked by acetylation. 6.5 ml acetic anhydride was added to the resin slurry followed by gently mixing for 30 min. The resin was then washed with 5 volumes of 0.1 M sodium phosphate, pH 7.5.

Bis(Carboxymethyl)cysteine coupling to bromoacetylated resin: The following reactions were conducted in reduced light conditions. The washed bromoacetylated resin cake was suspended in 1 resin volume of 0.1 M sodium phosphate, pH 7.5 to make a 50% resin slurry. The slurry was bubbled with nitrogen for 10 minutes to deaerate. 15 mmoles of bis(carboxymethyl)cysteine prepared as described in Example 2 was added and the pH was adjusted to 7.5 with 1 N sodium hydroxide. It was then mixed at room temperature for at least 2 hours. β-mercaptoethanol (14.3 M, 1.5 mL per liter resin) was added to the slurry and the incubation was continued for at least 30 minutes at room temperature to block unreacted bromoacetyl groups. The resin was then washed with 3 volumes phosphate buffered saline followed by 5 volumes of deionized water.

Nickel loading and capacity analysis: The N,N-bis(carboxymethyl)-L-cysteine prepared as described above was tested by first determining the ability of the material to chelate nickel as described in Example 1. This resin bound 12.0 μmole of nickel per ml of resin.

Protein binding and specificity testing: The use test for specific protein binding of poly histidine containing proteins by this resin was carried out as described in Example 1. The assay results demonstrated that the eluted protein from this one step isolation procedure using this unique chelate resin gave essentially homogeneous bacterial alkaline phosphatase.

EXAMPLE 4

Preparation and analysis of aminoethylamido-N,N-bis-(carboxymethyl)-L-cysteic acid coupled to the insoluble carrier agarose Preparation of L-cysteic acid methyl ester: A mixture of 1 g of L-cysteic acid, 8 ml of 4 N hydrochloric acid in dioxane and 30 ml dry methanol was placed in a bottle. The bottle was capped and stored for approximately 96 hours at room temperature. Thin layer chromatography of the clear solution [Analtech silica gel plates,n-butanol:ethyl acetate:acetic acid:water (1:1:1:1), chlorine/potassium iodide-starch reagent (Stewart. J. M and Young. J. D in Solid Phase Peptide Synthesis, Pierce Chemical Company, PP. 120 (1984)] indicated greater than 95% conversion of cysteic acid to the ester. Solvents were removed under vacuum to get 1.05 g of a sticky solid. Mass spec analysis gave the m/z for the major M⁺¹ ion as 184.3. Fragmentation of this ion gave the M⁺¹ ion of 123.9, which represents the loss of one of the carboxymethyl groups. The solids were used without further purification in the next step.

Aminoethylamido-N,N-bis-(carboxymethyl)-L-cysteic acid preparation: Triethylamine (10 ml) was added to a mixture of the 0.8 g of the above cysteic acid methyl ester in 12.5 ml of DMF in a bottle to get a clear solution. To this mixture 4.4 g of bromoacetic acid was added followed by approximately 15 ml of triethylamine until the pH was approximately 10. The solution became a solid mass. After a month at room temperature an additional 1.5 g of bromoacetic acid and 15 ml of DMF were added to the mixture. The pH of the mixture was adjusted to approximately 10 with triethylamine. Mass spec analysis gave the m/z of the major M⁻¹ ion as 298.2.

The above reaction mixture after 24 hours was filtered and the solids were washed with 20 ml of dimethyl formamide. Ethylenediamine (35 ml) was added to the brown filtrate and the solution was heated at 60° C. for 18 hours. The clear brown solution was evaporated under vacuum to an oil. 50 ml of water was added and evaporated again to an oil. The last step was repeated once more. Then 6.1 L of water was added to the brown oil and the solution was loaded onto a 100 ml column of DEAE Sephadex® (Pharmica Biotech). The column was washed with 800 ml of water. The product was eluted with a linear gradient with 1 L each of water and 0.1 N hydrochloric acid. The flow rate was 2 ml per minute. Fractions of 5 ml were collected. Fractions containing yellow product were assayed. Based on thin layer chromatography [Analtech silica gel plates, n-butanol:ethyl acetate: acetic acid:water (1:1:1:1), chlorine/potassium iodide-starch] the fractions containing the product were pooled and evaporated to dryness under vacuum to obtain 295 mg of light yellow foamy solid. Mass spec analysis gave the m/z of the major M⁺¹ of 328.5.

Preparation of aminoethylamido-N,N-bis-(carboxymethyl)-L-cysteic acid agarose: A solution of 221 mg of aminoethylamido-N,N-bis-carboxymethylcysteic acid prepared as above was dissolved in 3 ml of water and transferred to a glass bottle. To the bottle was added 10 ml 0.5 M sodium carbonate, followed by 8 g of wet epichlorohydrin activated Sepharose® CL 4B prepared as described in Example 3. The mixture was shaken gently at 60° C. for 24 hours. The resin was filtered and washed five times with 50 ml of water. The resin was stored in 20 ml 30% 200 proof ethanol at 4° C.

Nickel loading and capacity analysis: The aminoethylamido-N,N-bis-(carboxymethyl)-L-cysteic acid resin prepared as described above was tested as described in Example 1. This resin bound 15.6 μmole of nickel per ml of resin.

Protein binding and specificity testing: The use test for specific protein binding of poly histidine containing proteins by this resin was carried out as described in Example 1. The assay results demonstrated that the eluted protein from this one step isolation procedure using this unique chelate resin gave essentially homogeneous bacterial alkaline phosphatase.

EXAMPLE 5

Preparation and testing of N,N-bis(carboxymethyl)cysteine coupled to the soluble compound, bovine serum albumin Preparation of the soluble chelate: Bovine serum albumin (272 mg; BSA) at 10 mg/ml was dissolved in 0.1 M sodium phosphate, pH 7.2. Bromoacetic acid NHS ester (57 mg; 0.24 mmole) in 0.5 ml dimethyl formamide (DMF) was added to the solution and incubated for 2 hours at room temperature with stirring. The reaction mixture was desalted on a Sephadex® G-50 (Pharmacia Biotech) column equilibrated and run in 0.1 M sodium phosphate, pH 7.2. The column was monitored by absorbance at 280 nm. Fractions were combined that contained absorbance at 280 nm. They were then gently bubbled with Argon for 3 minutes. N,N-bis(carboxymethyl) cysteine (39 mg; 0.12 mmoles) was dissolved in 0.2 ml of 0.1 M sodium phosphate, pH 8.0 (as prepared in Example 3) and then added to the BSA solution, which was then bubbled with argon. The reaction mixture was incubated overnight at 4° C. The coupling efficiency was monitored by the 5,5'-dithio-bis(2-nitrobenzoic acid (DTNB) reaction and was determined to be at least 95%. The mixture was desalted on a Sephadex® G-50 (Pharmacia Biotech) column eluted with a buffer containing 10 mM 3-(N-morpholino)propanesulfonic acid (MOPS) and 0.15 M sodium chloride, pH 7.0. The soluble BSA-chelate was charged with 0.01 M nickel sulfate in a buffer of 10 mM MOPS and 0.15 M sodium chloride, pH 7.0. The final solution was desalted on a Sephadex® G-50 (Pharmacia Biotech) column. The desalted blue-colored BSA nickel chelate had absorbance peaks at 280 nm and 390 nm indicating that nickel was chelated to the conjugate.

Use testing the soluble bovine serum albumin carrier covalently attached to N,N-bis(carboxymethyl)cysteine: The BSA chelate prepared as described above was adsorbed to polystyrene microtiter wells using 5 ug/ml in 0.1 M sodium bicarbonate pH 9.6 overnight. The microtiter plate was washed three times with PBS with 0.05% Tween 20. The bound BSA chelate was charged with nickel by incubating the plate with 0.01 M nickel sulfate in MOPS pH 7.0 for 30 min at room temperature. The plate was washed with water three times. A model fusion protein, bacterial alkaline phosphatase, containing an N-terminal poly histidine tag was incubated in the BSA nickel chelate microtiter wells at various concentrations in the MOPS buffer. The plate was washed three times with the MOPS buffer to remove unbound protein. The alkaline phosphatase fusion protein was detected by incubation of the microtiter wells with an alkaline phosphatase enzyme substrate. The assay demonstrated a significant amount of chelate specific binding of the poly histidine fusion protein to the albumin nickel chelate.

The invention claimed is:

1. A metal chelating composition having the formula:

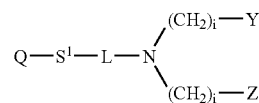

wherein

Q is a carrier;

$S^1$ is a spacer;

L is -A-T-CH(X)—;

A is an amide linkage;

T is a bond or substituted or unsubstituted alkyl or alkenyl;

X is —$(CH_2)_k$COOH;

k is an integer from 0 to 2;

Y is —COOH;

Z is —COOH; and i is an integer from 0 to 4.

2. The metal chelating composition of claim 1 wherein Q is agarose.

3. The metal chelating composition of claim 2 wherein $S^1$ consists of a chain of no more than about 25 atoms selected from the group consisting of carbon, nitrogen, oxygen and sulfur.

4. The metal chelating composition of claim 2 wherein $S^1$ consists of a chain of no more than about 25 atoms selected from the group consisting of carbon, oxygen and sulfur.

5. The metal chelating composition of claim 2 wherein $S^1$ consists of a chain of no more than about 15 atoms selected from the group consisting of carbon, oxygen and sulfur and T is —$(CH_2)_n$— wherein n is 0 to 6.

6. The metal chelating composition of claim 1 wherein the carrier is selected from the group consisting of agarose, cellulose, methacrylate copolymers, polystyrene, polypropylene, paper, polyamide, polyacrylonitrile, polyvinylidene, polysulfone, nitrocellulose, polyester, polyethylene, silica, glass, latex, plastic, gold, iron oxide, polyacrylamide, nucleic acid, lipids, liposomes, synthetic soluble polymers, proteins, polyamino acids, albumin, antibodies, enzymes, streptavidin, peptides, hormones, chromogenic dyes, fluorescent dyes, flurochromes, and polysaccharides.

7. The metal chelating composition of claim 1 wherein $S^1$ consists of a chain of no more than about 25 atoms selected from the group consisting of carbon, nitrogen, oxygen and sulfur.

8. The metal chelating composition of claim 1 wherein $S^1$ consists of a chain of no more than about 25 atoms selected from the group consisting of carbon, oxygen and sulfur.

9. The metal chelating composition of claim 1 wherein $S^1$ consists of a chain of no more than about 15 atoms selected from the group consisting of carbon, oxygen and sulfur and T is —$(CH_2)_n$— wherein n is 0 to 6.

10. A metal chelate comprising a chelate of a metal and the metal chelating composition of claim 1.

11. The metal chelate of claim 10 wherein the metal is selected from the group consisting of Ni, Hg, Ga, Cu, Ru, Co, Cd, Mg, Mn, Ti, In, Zn, Tc, Rh, Pd, Re, Fe, Au, Pb, and Bi.

12. The metal chelate of claim 10 wherein the metal is selected from the group consisting of Fe, Cu, Co, Au, and Ni.

13. The metal chelate of claim 10 wherein the metal is nickel.

14. A process for the purification or detection of a composition, the process comprising contacting the composition with a metal chelate of claim 10.

15. The process of claim 14 wherein the composition is a polypeptide containing at least two histidine residues.

16. The process of claim 14 wherein the composition is a polypeptide containing at least six histidine residues.

17. The process of claim 14 wherein the composition is a protein, phosphoprotein, peptide, phosphopeptide, nucleic acid, oligonucleotide, drug, or synthetic or natural product having an affinity for a metal chelate.

18. A process for the preparation of a mono- or dicarboxylated amine, the process comprising combining an amine and an oxoacid in the presence of a reducing agent, the amine having the formula $R^2R^3NH$ wherein $R^2$ is hydrocarbyl or substituted hydrocarbyl and $R^3$ is hydrogen, hydrocarbyl or substituted hydrocarbyl.

19. The process of claim 18 wherein the oxoacid is glyoxylic acid.

20. The process of claim 18 wherein the reducing agent is a pyridine-borane complex, dimethylborane, trimethylborane, or sodium cyanoborohydride.

21. The process of claim 18 wherein the amine is an amino acid.

22. The process of claim 18 wherein the amine is an amino acid selected from the group consisting of cystine, homocystine, cysteine, homocysteine, aspartic acid, cysteic acid or an ester thereof.

23. The process of claim 18 wherein the amine is cystine, cysteine, cysteic acid or an ester thereof.

* * * * *